(12) United States Patent
Delapierre et al.

(10) Patent No.: US 8,592,619 B2
(45) Date of Patent: Nov. 26, 2013

(54) BIFUNCTIONAL MOLECULES COMPRISING A CYCLOALKYNE OR HETEROCYCLOALKYNE GROUP AND A REDOX GROUP

(75) Inventors: Guillaume Delapierre, Vif (FR); Regis Barattin, Grenoble (FR); Aude Bernardin, Lailly-en-Val (FR); Isabelle Texier-Nogues, Grenoble (FR)

(73) Assignee: Commissariat a L'Energie Atomique et aux Enerigies Alternatives, Paris (FR)

( * ) Notice: Subject to any disclaimer, the term of this patent is extended or adjusted under 35 U.S.C. 154(b) by 224 days.

(21) Appl. No.: 13/257,365

(22) PCT Filed: Mar. 16, 2010

(86) PCT No.: PCT/FR2010/000221
§ 371 (c)(1),
(2), (4) Date: Nov. 2, 2011

(87) PCT Pub. No.: WO2010/106245
PCT Pub. Date: Sep. 23, 2010

(65) Prior Publication Data
US 2012/0037871 A1    Feb. 16, 2012

(30) Foreign Application Priority Data
Mar. 18, 2009 (FR) .................... 09 01256

(51) Int. Cl.
*C07F 17/02* (2006.01)
*H01L 45/00* (2006.01)
*H01L 21/312* (2006.01)

(52) U.S. Cl.
USPC ........ 556/144; 438/780; 257/1; 257/E21.259; 257/E45.002

(58) Field of Classification Search
USPC ............... 556/144; 438/780; 257/1, E21.259, 257/E45.002
See application file for complete search history.

(56) References Cited

U.S. PATENT DOCUMENTS 8,431,558 B2 * 4/2013 Bertozzi et al. ............... 514/183
2008/0280047 A1 11/2008 Bocian et al.

FOREIGN PATENT DOCUMENTS

WO  2005 086826  9/2005

OTHER PUBLICATIONS

U.S. Appl. No. 13/257,365, filed Nov. 2, 2011, Delapierre, et al.
U.S. Appl. No. 13/257,419, filed Oct. 25, 2011, Barattin, et al.
U.S. Appl. No. 13/257,326, filed Sep.19, 2011, Bernardin, et al.
International Search Report Issued May 26, 2010 in PCT/FR10/000221 filed Mar. 16, 2010.

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

The invention relates to compounds comprising a cycloalkyne or heterocycloalkyne group and a redox group. Said compounds are of general formula (I) wherein Z is a cycloalkyne or heterocycloalkyne with at least 8 links, optionally substituted by a halogen atom or a linear or branched C1 to C5 alkyl, A is an organic structure having oxidation-reduction properties, and B is an organic link between the cycloalkyne or heterocycloalkyne cycle and the organic structure A. The invention is especially applicable to the field of molecular electronics.

10 Claims, No Drawings

BIFUNCTIONAL MOLECULES COMPRISING A CYCLOALKYNE OR HETEROCYCLOALKYNE GROUP AND A REDOX GROUP

This application is a 371 of PCT/FR2010/000221, filed Mar. 16, 2010.

The invention relates to compounds comprising a cycloalkyne or heterocycloalkyne group and a redox group.

The invention also relates to the use of these compounds for functionalizing a substrate made of an inorganic material, and also to a molecular memory hybrid system comprising such a substrate.

The functionalization of an inorganic substrate with organic molecules is proving to be of ever-increasing interest in numerous technical fields.

In particular, in the field of molecular electronics, research is increasingly focused on compounds for functionalizing semiconductor substrates, in particular made of silicon and germanium.

There is in this field a particular demand for substrates for molecular memory hybrid systems.

It has already been proposed to use redox molecules containing an alkyne function used for functionalizing semiconductor substrates and for developing molecular memory hybrid systems (studies by D. Bocian et al.: *J. Org. Chem.*, 2006, 71, 1156-1171; patent WO 2005/086826 A2).

This type of molecular memory device uses the properties of redox molecules for storing information.

More specifically, the writing of data is performed during the oxidation of the redox molecule and the erasing of data is performed during the reduction reaction of the redox molecule.

The invention is directed toward providing novel compounds comprising two functionalities, one of them being formed by a group (a molecule) with redox properties and the other being an alkyne functionality.

To this end, the invention proposes compounds of general formula I below:

Formula I in which
  Z is a cycloalkyne or a heterocycloalkyne that is at least 8-membered, optionally substituted with a halogen atom or a linear or branched $C_1$ to $C_5$ alkyl,
  A is an organic structure having redox properties,
  B is an organic link between the cycloalkyne or the heterocycloalkyne and the organic structure A.

Preferably, Z is an unsubstituted cycloalkyne or heterocycloalkyne that is between 8- and 12-membered, inclusive.

In the invention, the term "8-membered to 12-membered" means a ring comprising between 8 and 12 atoms, which are carbon atoms in the cycloalkyne and 8 to 12 carbon atoms or heteroatoms such as O, N and S, in the heterocycloalkyne.

The atoms of the substituent, when present, are not included for the calculation of the chain members.

More preferably, Z is an unsubstituted cyclooctyne.

The organic structure A has redox properties. In the invention, an organic molecule is said to have "redox properties" when it is capable of losing or gaining electrons reversibly and of remaining stable in the corresponding neutral and charged states. Taken in the context of molecular memories, where the supply and loss of electrons takes place by means of an electrical voltage, this definition excludes any organic function that can be chemically reduced or oxidized.

Preferably, in the compounds of the invention, A is chosen from a ferrocene molecule, a porphyrin molecule, an anthracene molecule, a naphthalene molecule, a fullerene molecule and a polyoxometallate molecule.

Preferably also, in the compounds of the invention, B is chosen from a linear or branched, saturated or unsaturated $C_1$ to $C_{30}$ alkyl of 1 to 30 carbons inclusive, optionally comprising heteroatoms and/or amide and/or ester functions; a 5- to 6-carbon aryl; and a 5- to 6-carbon heteroaryl.

Still preferably, in the compounds of the invention, the substituent "—B-A" is in the α position relative to the triple bond of the cycloalkyne or heterocycloalkyne ring.

A compound that is particularly preferred in the invention has the formula I-A below:

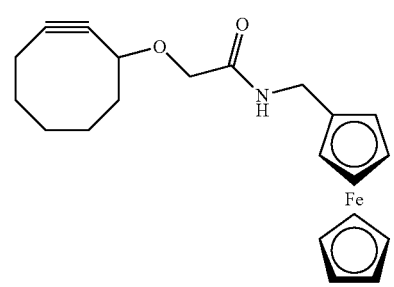

Formula I-A

Another compound that is particularly preferred in the invention is the compound of formula I-B below:

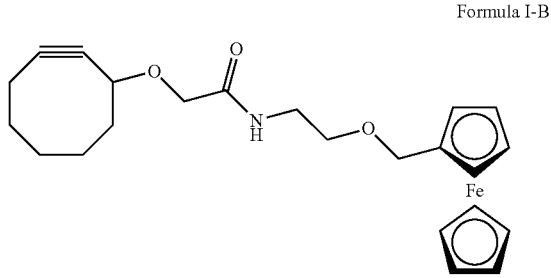

Formula I-B

The invention also proposes the use of at least one compound of formula I according to the invention for the functionalization of an inorganic substrate.

Preferably, the substrate is made of a semiconductor material.

More preferably, the substrate is made of silicon.

The invention also proposes a molecular memory hybrid system, characterized in that it comprises a semiconductor substrate functionalized with at least one compound of general formula I according to the invention.

According to the invention, the silicon or germanium surface of the system was functionalized with molecules with redox properties. The functionalization takes place by means of the alkyne function that reacts with the hydrogenated substrate according to a hydrosilylation reaction. The system obtained then contains a layer of redox molecules at its surface. The various available redox states are then used to store the information on the surface, by varying the voltage applied to the system: by applying a voltage corresponding to the oxidation potential of the grafted molecules, the surface becomes charged (writing of data); by returning to the initial state (reduction), the surface once again becomes neutral (erasing of data).

The invention will be understood more clearly and other characteristics and advantages thereof will emerge more clearly on reading the explanatory description that follows.

The novel compounds of the invention comprise two groups of interest:

a group, noted as Z, composed of a cycloalkyne or heterocycloalkyne part, which will allow the compound to be bonded to the surface of an inorganic substrate, in particular a semiconductor, preferably silicon, by coupling the (hetero)cycloalkyne, either, for example, with an azido group ($N_3$) created on the substrate, or by 1,3-dipolar cyclization (Huisgen), or alternatively by direct grafting of the cycloalkyne onto a non-oxidized surface of the substrate by hydrosilylation, and a group, noted as A, with redox properties.

In the compounds of the invention, these two groups are connected via a spacer, noted as B.

The group Z may be a cycloalkyne or a heterocycloalkyne that is at least 8-membered, preferably between 8-membered and 12-membered, and is optionally substituted with a halogen such as F, Cl, Br or I or with a linear or branched $C_1$ to $C_5$ alkyl.

Preferably, Z is an unsubstituted cycloalkyne or heterocycloalkyne.

More preferably, Z is a cyclooctyne.

The redox molecule (the group A) is a molecule that is capable of accepting or giving one or more electrons.

Examples that may be mentioned include ferrocene, porphyrins, anthracene, naphthalene, fullerenes and polyoxometallates.

Ferrocene is most particularly preferred.

As regards the group B, it is an organic link between the cyclooctyne and the redox structure A.

This organic link may be a linear or branched, saturated or unsaturated alkyl chain of $C_1$ to $C_{30}$ inclusive, optionally comprising heteroatoms, more particularly oxygen or nitrogen atoms and/or amide and/or ester functions. This organic link may also be a $C_5$ to $C_6$ aryl or a $C_5$ to $C_6$ heteroaryl.

This organic link may be attached at any position on the cyclooctyne ring.

However, preferably, it will be attached a to the triple bond of the cyclooctyne ring.

A compound that is most preferred according to the invention is a compound of formula I-A below:

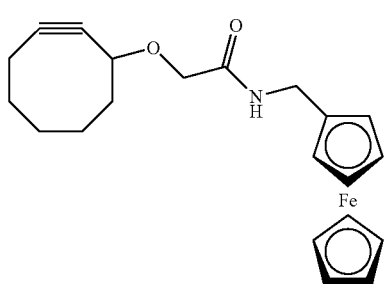

Formula I-A

Another compound according to the invention is a compound of formula I-B below:

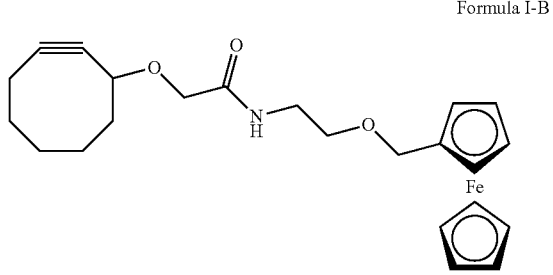

Formula I-B

The compounds of the invention may be used for the functionalization of a substrate made of an organic material, and more particularly of a substrate made of a semiconductor material, in particular made of silicon or germanium.

Preferably, the substrate is made of silicon.

This substrate may then be used in a molecular memory hybrid system.

Thus, the molecular memory hybrid system according to the invention comprises a substrate made of a semiconductor material, preferably made of silicon, functionalized with compounds of general formula I.

The functionalization of the substrate may take place, in particular, either by coupling the (hetero)cycloalkyne, preferably a cyclooctyne, with an azido group ($N_3$), or by 1,3-dipolar cyclization, i.e. via a Huisgen reaction.

In the case of coupling with an azido group, an azido group is first bonded to the surface of the silicon substrate. This azido group will then react with the triple bond of the (hetero)cycloalkyne ring, preferably a cyclooctyne, according to scheme 1 below:

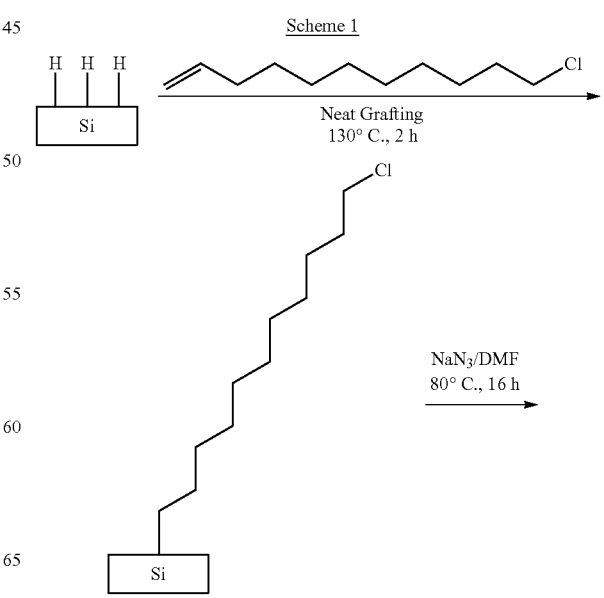

Scheme 1

-continued

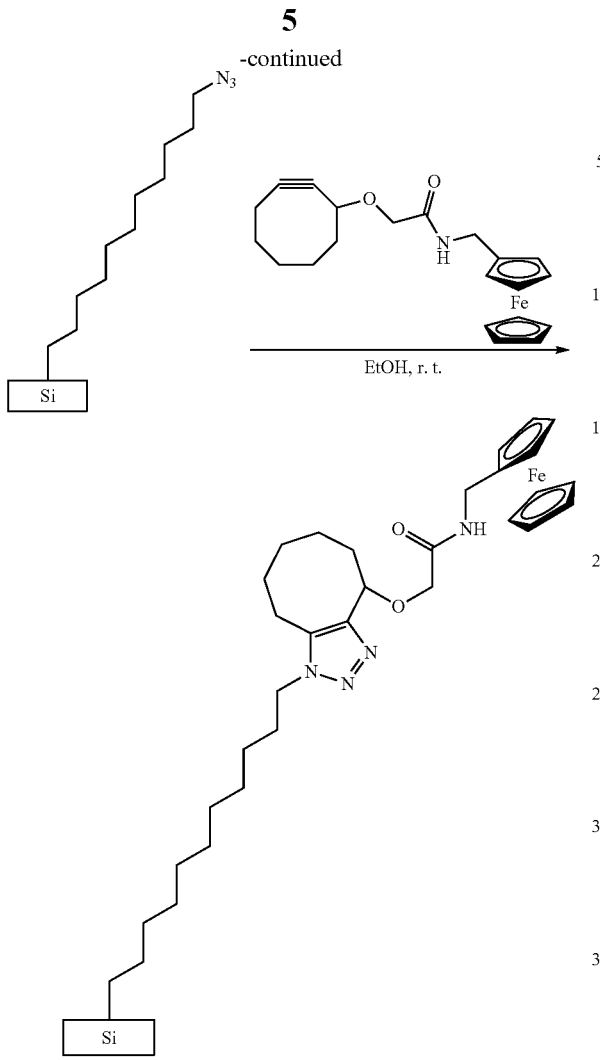

EtOH, r. t.

The functionalization of the substrate may also be performed by direct grafting of the (hetero)cycloalkyne, preferably a cyclooctyne, onto a non-oxidized silicon surface via hydrosilylation.

In order to have the invention more clearly understood, implementation examples will now be described, as purely illustrative and nonlimiting examples.

EXAMPLE 1

Synthesis of the Compound of Formula I-A

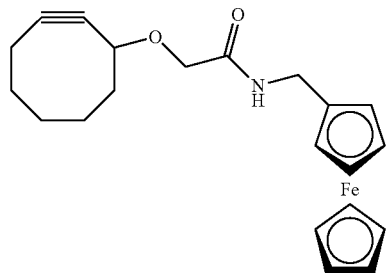

Formula I-A

1. Synthesis of 8,8-dibromobicyclo[5.1.0]octane

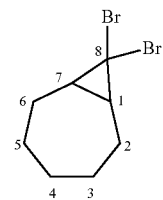

3.65 g of cycloheptene (i.e. 38 mmol) are placed in a dry round-bottomed flask, under argon, followed by 8.52 g of t-BuOK (i.e. 76 mmol, 2 eq.) and 9 mL of predistilled pentane. The cream-yellow solution obtained is stirred vigorously and placed in an ice/salt bath. Next, 4.9 mL of bromoform (i.e. 57 mmol, 1.5 eq.) are added dropwise. During the first additions, a relatively violent evolution of gas is observed, and then, as the addition proceeds, the solution turns brown-ochre. During the addition, about a further 5 mL of pentane were added to allow correct stirring of the solution. Once the addition is complete, the mixture is left to return to room temperature overnight, under argon and with vigorous stirring.

About 50 mL of water are then added and the pH is neutralized with 1M HCl. The organic and aqueous phases are separated; the aqueous phase is extracted with 3×20 mL of pentane and the pentane phase is washed with 3×20 mL of water. The organic phase is then dried over $MgSO_4$ and the solvent evaporated off under vacuum. An orange-yellow oil is obtained in a mass m=10.814 g.

The product is then purified by simple filtration on silica, using cyclohexane/5% EtOAc as eluent. A colorless oil in a total mass of 9.100 g is obtained after purification, i.e. in a yield of 90% (litt. 52-65% for 9,9-dibromobicyclo[6.1.0]nonane).

$R_f$ (cyclohexane 95/EtOAc 5)=0.85;

$^1H$ NMR ($CDCl_3$, 200 MHz): δ (ppm) 1.05-1.22 (m, 3H); 1.34 (qq, J=1-7.5 Hz, 2H); 1.68 (ddd, J=1.5-4-10.5 Hz, 2H); 1.76-1.92 (m, 3H); 2.23 (dtq, J=14-6-1 Hz, 2H);

$^{13}C$ NMR ($CDCl_3$, 50 MHz): δ (ppm) 40.7 ($C_8$ quat.); 34.8 (2, $C_{1-7}$); 32.2 ($C_4$); 28.9 (2, $C_{2-6}$); 27.9 (2, $C_{3-5}$);

Mass: $ESI^+$ m/z $[M+H_2O+H]^+$=284.4 for 284.9; $[M+HBr+Na]^+$=368.5 for 369.93

IR: ν ($cm^{-1}$) 2921 $ν_{CH}$; 2853 $ν_{CH2}$; 1457 $δ_{CH}$; 1354 $δ_{CH\ tertiary}$; 735 $ν_{CBr}$.

2. Synthesis of methyl 2-bromocyclooctene-3-glycolate

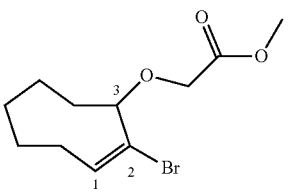

To a solution of 8,8-dibromobicyclo[5.1.0]octane (2.5 g, i.e. 9.3 mmol) and of methyl glycolate (6.32 mL, i.e. 83.9 mmol) dissolved in 5 mL of anhydrous toluene in a dry round-bottomed flask, under Ar and protected from light by a film of aluminum, are added 3.85 g of silver perchlorate (i.e. 18.6 mmol). The reaction is stirred for 1 hour 30 minutes at room temperature, and the silver salts are then filtered off on a sinter and washed with EtOAc. The solution is concentrated under vacuum to give a viscous brown oil, which is purified by chromatography on silica gel (2-150 EtOAc in cyclohexane) to give the product in the form of a yellow oil of mass m=1.6 g, i.e. 65% yield.

$R_f$ (petroleum ether/5% EtOAc)=0.25;

$^1$H NMR (CDCl$_3$, 200 MHz): δ (ppm) 0.7-2.2 (m, 8H); 2.28 (m, 1H); 2.70 (ddd, J=5-11.5-23.5 Hz, 1H); 3.72 (s, 3H, OMe); 3.94 (d, $J_{9-9'}$=16.5 Hz, 1H, $H_9$); 4.10 (dd, $J_{3-4}$=5 Hz, $J_{3-4'}$=10 Hz, 1H, $H_3$); 4.23 (d, $J_{9-9'}$=16.5 Hz, 1H, $H_{9'}$); 6.20 (dd, $J_{1-8}$=4 Hz, $J_{1-8}$=11.5 Hz, 1H, $H_1$);

$^{13}$C NMR (CDCl$_3$, 50 MHz): 26.2; 28.0; 33.4; 36.5; 39.3 ($C_{4-8}$); 51.8 ($C_3$); 65.4 ($C_{11}$); 84.8 ($C_9$); 131.4 ($C_2$ quat.); 133 ($C_1$); 170.7 ($C_{10}$ quat.);

Mass: ESI$^+$ m/z [M+H]+=277.6-279.6; [M+Na]+=299.6-306.1; [2M+H]+=553.0-555.0-557.0; [2M+Na]+=575.0-576.9-578.8;

IR: ν (cm$^{-1}$) 2931 $ν_{CH}$; 2856 $ν_{CH2}$; 1754 $ν_{C=O}$; 1445 $ν_{C=C\ trans}$; 1132 $ν_{COC\ ether}$.

3. Synthesis of cyclooct-1-yne-3-glycolic acid

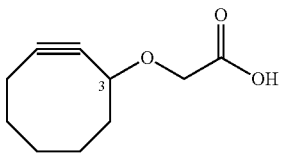 [SMILES: O=C(O)COC1C#CCCCCC1]

To 250 mg of methyl 2-bromocyclooctene-3-glycolate (i.e. 0.90 mmol) is added a 0.5M solution of sodium methoxide in methanol. The mixture is stirred for 2 days at room temperature.

The reaction is acidified with 1M HCl and then extracted with EtOAc, dried over MgSO$_4$, and the solvents are evaporated off. The product is purified on silica gel with EtOAc and is obtained in the form of a yellow oil in a mass of 120 mg, i.e. 80% yield.

$^1$H NMR (CDCl$_3$, 200 MHz): δ (ppm) 1.3-2.3 (m, 10H); 4.45 (d, $J_{9-9'}$=17 Hz, 1H, $H_9$); 4.50 (m, 1H, $H_3$); 4.58 (d, $J_{9-9'}$=17 Hz, 1H, $H_{9'}$);

$^{13}$C NMR (CDCl$_3$, 50 MHz): δ (ppm)

Mass: ESI$^+$ m/z

4. Synthesis of Ferrocene-Cyclooctyne of Formula I-A

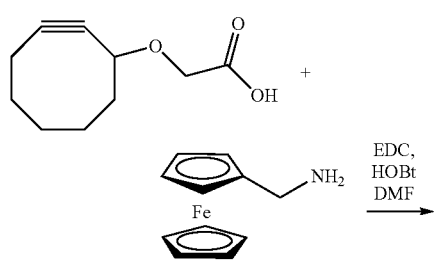

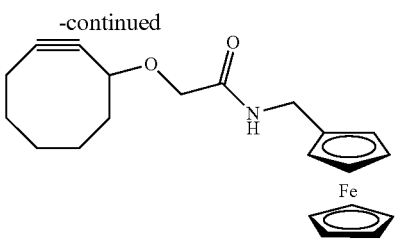

To a solution of cyclooct-1-yne-3-glycolic acid (33 mg, i.e. 0.18 mmol) in 2 mL of anhydrous DMF are added 41 mg of EDC (i.e. 0.21 mmol) and 28 mg of HOBt (i.e. 0.21 mmol). After stirring at room temperature under argon for 15 minutes, a solution of ferrocene-methylamine (45 mg, i.e. 0.21 mmol) in 0.8 mL of anhydrous DMF is added dropwise. Stirring is continued for 24 hours.

After addition of 10 mL of water, the reaction mixture is extracted with dichloromethane. The organic phase is dried over anhydrous Na$_2$SO$_4$, filtered and concentrated under vacuum. The product is purified on silica gel (99/1: DCM/MeOH) and is obtained in the form of a yellow oil (21 mg, i.e. 30% yield).

The compound of formula I-A was dissolved and its redox activity was tested by cyclic voltammetry using a three-electrode system.

The working electrode is a platinum electrode, the reference electrode is a saturated calomel electrode and the counterelectrode is a platinum electrode.

The electrolyte used is a 1M solution of Bu$_4$NPF$_6$ in propylene carbonate.

The cyclic voltammetry measurement was taken at a scan speed of 500 mV/s.

An oxidation peak at 0.5V and a reduction peak at 0.35V are identified.

It is thus confirmed that the modification of the ferrocene with cyclooctyne does not destroy the redox activity of ferrocene.

EXAMPLE 2

Functionalization of a Silicon Surface with the Compound of Formula I-A

A silicon surface comprising an azido function (N$_3$) was prepared in 2 steps from a hydrogenated silicon surface.

Next, a 1,3-dipolar cyclization reaction (Huisgen reaction) between this azido function and the compound of formula I-A made it possible to immobilize the ferrocene structure on a silicon substrate.

More specifically, the following three steps were performed:

1—Hydrosilylation by Neat Grafting of 11-chloroundec-1-ene

In a sealed tube, a silicon surface hydrogenated beforehand by treatment with 1% HF is covered with 0.5 mL of 11-chloroundec-1-ene. The reaction medium is heated at 130° C. for 2 hours by immersion in a graphite bath. After cooling to room temperature, the surface is washed and sonicated successively in acetone, ethanol and dichloromethane.

2—Formation of the Azido Surface

The chlorinated surface synthesized previously is introduced into a saturated solution of NaN$_3$ (0.25 g) in DMF (20 mL). The reaction medium is heated at 80° C. for 16 hours under argon. After cooling to room temperature, the surface is washed and sonicated successively in water, acetone, ethanol and dichloromethane.

3—Coupling of the Cyclooctyne-Ferrocene

The azido surface prepared previously is introduced into a 1 mM solution of cyclooctyne-ferrocene in ethanol. The reaction medium is stirred at room temperature under an argon atmosphere for 24 hours. The surface is then washed and sonicated in dichloromethane, and dried under argon.

The redox activity of the compound of formula I-A on this surface was checked by cyclic voltammetry.

The cyclic voltammetry measurements were taken using a three-electrode system: the working electrode is the silicon substrate functionalized with the compound of formula I-A, the reference electrode is a saturated calomel electrode and the counterelectrode is a platinum electrode. The electrolyte used is a 1M solution of $Bu_4NPF_6$ in propylene carbonate. The cyclic voltammetry measurements were taken at scan speeds ranging from 50 mV/s to 750 mV/s.

The ΔE(ox/red) is relatively large, about 0.8V, on account of the length of the spacer between the redox molecule and the silicon semiconductor surface.

EXAMPLE 3

Functionalization of a Silicon Support with the Compound of Formula I-A

In this example, it is demonstrated that it is possible to directly graft the compound of formula I-A by heating on a hydrogenated silicon surface.

Thus, the compound of formula I-A was grafted directly onto a hydrogenated silicon surface in the following manner.

A silicon surface hydrogenated beforehand by treatment with 1% HF is placed in a 1 mM solution of cyclooctyne-ferrocene in mesitylene. The reaction medium is heated (100° C./130° C./180° C.) under an argon atmosphere for 2 hours. After cooling to room temperature, the surface is washed and sonicated in dichloromethane, and dried under argon.

The three substrates obtained were subjected to cyclic voltammetry measurements.

The cyclic voltammetry measurements were taken using a three-electrode system: the working electrode is the silicon substrate studied, the reference electrode is a saturated calomel electrode and the counterelectrode is a platinum electrode. The electrolyte used is a 1M solution of $Bu_4NPF_6$ in propylene carbonate. The cyclic voltammetry measurements were taken at scan speeds ranging from 10 mV/s to 1000 mV/s.

It is observed that once the grafting takes place at 130° C., efficient grafting of the molecule is obtained, which makes it possible to observe the redox activity of ferrocene on the silicon surface.

At 130° C., and at a scan speed of 10 mV/s, the ΔE is 109 mV.

At a scan speed of 20 mV/s, the ΔE is 119 mV.

At a scan speed of 500 mV/s, the ΔE is 317 mV.

The grafting density, i.e. the number of redox molecules per unit surface area, was evaluated by electrochemistry as $7.8 \times 10^{-11}$ molecules·$cm^{-2}$ (at a scan speed of 500 mV/s).

As regards the grafting performed at 180° C., the cyclic voltammetry measurement at a scan speed of 10 mV/s shows that the ΔE(ox/red) is 59 mV.

At a scan speed of 20 mV/s, the ΔE(ox/red) is 59 mV.

At a scan speed of 100 mV/s, the ΔE(ox/red) is 129 mV.

At a scan speed of 500 mV/s, the ΔE(ox/red) is 228 mV.

In this case, the grafting density was evaluated by electrochemistry as $2.3 \times 10^{-11}$ molecules·$cm^{-2}$ (at a scan speed of 500 mV/s).

The ΔE(ox/red) and grafting density values for the graftings performed at 130° C. and 180° C. show that the grafting at 180° C. is more efficient. Specifically, the grafting density is increased by a factor of 3 and the small difference between the oxidation potential and the reduction potential is smaller, which is a sign of less reoxidation of the substrate and thus better grafting. However, it should be noted that it is not necessary to perform activation at such a high temperature, since the grafting can nevertheless be performed at 130° C.

EXAMPLE 4

Synthesis of the Compound of Formula I-B

Formula I-B

To a solution of cyclooct-1-yne-3-glycolic acid (34 mg, i.e. 0.19 mmol) in 2 mL of anhydrous DMF are added 41 mg of EDC (i.e. 0.21 mmol) and 28 mg of HOBt (i.e. 0.21 mmol). After stirring at room temperature under argon for 15 minutes, the 2-aminoethyl-ferrocenyl methyl ether (70 mg, i.e. 0.21 mmol) is added. Stirring is continued for 24 hours.

After evaporating off the solvent under vacuum, the residue is redissolved in dichloromethane. The organic phase is washed with water, dried over anhydrous $Na_2SO_4$, filtered and concentrated under vacuum. The product is purified on silica gel (98/2: DCM/MeOH) and is obtained in the form of a yellow oil (31 mg, i.e. 39% yield).

The compound of formula I-B was dissolved, and its redox activity was tested by cyclic voltammetry using a three-electrode system.

The working electrode is a platinum electrode, the reference electrode is a saturated calomel electrode and the counterelectrode is a platinum electrode.

The electrolyte used is a 1M solution of $Bu_4NPF_6$ in propylene carbonate.

The cyclic voltammetry measurement was taken at a scan speed of 500 mV/s.

An oxidation peak at 0.448 V and a reduction peak at 0.317 V are identified.

It is thus confirmed that modification of ferrocene with cyclooctyne does not destroy the redox activity of ferrocene.

EXAMPLE 5

Functionalization of a Silicon Support with the Compound of Formula I-B

In this example, it is demonstrated that it is possible to graft directly the compound of formula I-B by heating on a hydrogenated silicon surface.

Thus, the compound of formula I-B was grafted directly onto a hydrogenated silicon surface in the following manner.

A silicon surface hydrogenated beforehand by treatment with 1% HF is introduced into a 1 mM solution of cyclooctyne-ferrocene in mesitylene. The reaction medium is heated (100° C./130° C./180° C.) under an argon atmosphere for 2 hours. After cooling to room temperature, the surface is washed and sonicated in dichloromethane, and dried under argon.

The three substrates obtained were subjected to cyclic voltammetry measurements.

The cyclic voltammetry measurements were taken using a three-electrode system: the working electrode is the silicon substrate studied, the reference electrode is a saturated calomel electrode and the counterelectrode is a platinum electrode. The electrolyte used is a 1M solution of $Bu_4NPF_6$ in propylene carbonate. The cyclic voltammetry measurements were taken at scan speeds ranging from 10 mV/s to 1000 mV/s.

It is found that once the grafting takes place at 100° C., efficient grafting of the molecule is obtained, which makes it possible to observe the redox activity of ferrocene on the silicon surface.

At 100° C., and at a scan speed of 10 mV/s, the ΔE is 111 mV.

At a scan speed of 50 mV/s, the ΔE is 201 mV.
At a scan speed of 100 mV/s, the ΔE is 262 mV.
At a scan speed of 500 mV/s, the ΔE is 362 mV.
At 130° C., and at a scan speed of 10 mV/s, the ΔE is 91 mV.
At a scan speed of 500 mV/s, the ΔE is 111 mV.
At a scan speed of 2000 mV/s, the ΔE is 141 mV.

The grafting density, i.e. the number of redox molecules per unit surface area, was evaluated by electrochemistry as $3.9 \times 10^{-11}$ molecules·cm$^{-2}$ (at a scan speed of 500 mV/s).

As regards the grafting performed at 180° C., the cyclic voltammetry measurement at a scan speed of 100 mV/s shows that the ΔE(ox/red) is 70 mV.

At a scan speed of 500 mV/s, the ΔE(ox/red) is 121 mV.
At a scan speed of 1000 mV/s, the ΔE(ox/red) is 151 mV.
At a scan speed of 2000 mV/s, the ΔE(ox/red) is 181 mV.

In this case, the grafting density was evaluated by electrochemistry as $1.0 \times 10^{-11}$ molecules·cm$^{-2}$ (at a scan speed of 500 mV/s).

In the case of compound I-B, the spacer between the cyclooctyne and the redox molecule (ferrocene) is longer. This factor appears to allow more efficient grafting (by reducing the steric strain) since the grafting is effective at and above 100° C. At this temperature, the grafting appears, however, less efficient since greater reoxidation of the substrate is observed (ΔE(ox/red) greater). In contrast, at and above 130° C., the results show (both as regards the ΔE(ox/red) and as regards the grafting density) that the grafting is very efficient. In this case, it would therefore appear that there is sufficient thermal activation to allow the grafting and that there is better organization of the layer formed due to the longer spacer accompanying a lower reoxidation of the substrate.

The invention claimed is:

1. A compound of general formula I below:

Formula I

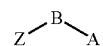

in which
Z is a cycloalkyne or a heterocycloalkyne that is at least 8-membered, optionally substituted with a halogen atom or a linear or branched $C_1$ to $C_5$ alkyl,
A is selected from the group consisting of a ferrocene molecule, a porphyrin molecule, an anthracene molecule, a naphthalene molecule, a fullerene molecule and a polyoxometallate molecule,
B is a linear or branched, saturated or unsaturated alkyl of $C_1$ to $C_{30}$ inclusive, optionally comprising heteroatoms and/or amide and/or ester functions, or a $C_5$ to $C_6$ aryl, a $C_5$ to $C_6$ heteroaryl.

2. The compound as claimed in claim 1, in which Z is a cycloalkyne or a heterocycloalkyne that is 8-membered to 12-membered, inclusive.

3. The compound as claimed in claim 1, in which Z is a cyclooctyne.

4. The compound of general formula I as claimed in claim 1, wherein the substituent —B-A is in the position α to the triple bond of the cycloalkyne or of the heterocycloalkyne.

5. The compound as claimed in claim 1, wherein the compound has the formula I-A below:

Formula I-A

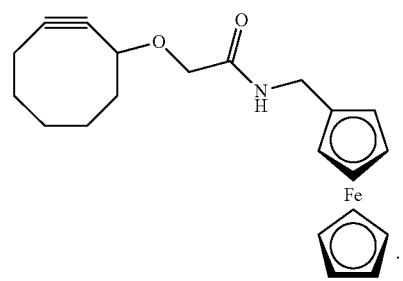

6. The compound as claimed in claim 1, wherein the compound has the formula I-B below:

Formula I-B

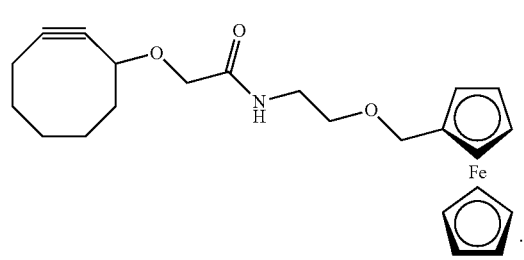

7. A method of functionalizing an inorganic substrate comprising reacting the compound of claim 1 with an inorganic substrate.

8. The method of claim 7, wherein the substrate comprises a semiconductor material.

9. The method of claim 7, wherein the substrate comprises silicon.

10. A molecular memory hybrid system, comprising a semiconductor substrate functionalized with at least one compound of general formula I as claimed in claim 1.

* * * * *